US009044615B2

(12) United States Patent
Hou et al.

(10) Patent No.: US 9,044,615 B2
(45) Date of Patent: Jun. 2, 2015

(54) METHOD AND SYSTEM FOR VALIDATING LOCAL CAPTURE IN MULTISITE PACING DELIVERY

(71) Applicant: Pacesetter, Inc., Sylmar, CA (US)

(72) Inventors: Wenbo Hou, Valencia, CA (US); Stuart Rosenberg, Castaic, CA (US); Xiaoyi Min, Camarillo, CA (US); Allen Keel, San Francisco, CA (US)

(73) Assignee: PACESETTER, INC., Sylmar, CA (US)

( * ) Notice: Subject to any disclaimer, the term of this patent is extended or adjusted under 35 U.S.C. 154(b) by 22 days.

(21) Appl. No.: 13/968,233

(22) Filed: Aug. 15, 2013

(65) Prior Publication Data
US 2015/0051661 A1    Feb. 19, 2015

(51) Int. Cl.
*A61N 1/37*    (2006.01)

(52) U.S. Cl.
CPC .................................... *A61N 1/3712* (2013.01)

(58) Field of Classification Search
None
See application file for complete search history.

(56) References Cited

U.S. PATENT DOCUMENTS

| 7,177,689 B2 | 2/2007 | Ternes et al. |
| 7,286,876 B2 | 10/2007 | Yonce et al. |
| 7,412,287 B2 | 8/2008 | Yonce et al. |
| 8,209,010 B2 | 6/2012 | Ryu et al. |
| 8,265,755 B2 | 9/2012 | Min |
| 8,509,890 B2 * | 8/2013 | Keel et al. ............... 607/9 |
| 2003/0083711 A1 | 5/2003 | Yonce et al. |
| 2011/0098770 A1 | 4/2011 | Ryu et al. |
| 2011/0196442 A1 | 8/2011 | Ryu et al. |
| 2012/0271371 A1 | 10/2012 | Keel et al. |

FOREIGN PATENT DOCUMENTS

WO    2004026398 A1    4/2004

* cited by examiner

*Primary Examiner* — Paula J Stice

(57) ABSTRACT

A method for use with an implantable system including a lead having multiple electrodes implantable proximate to a patient's left ventricular (LV) chamber includes simultaneously delivering pacing pulses over corresponding pacing vectors defined by electrodes proximate to the LV chamber. The method includes recording evoked responses responsive to the pacing pulses that are measured over separate corresponding sensing channels. The method also includes comparing the evoked responses to a template that represents local capture of a local LV tissue region along one or more of the corresponding pacing vectors. The comparison is used to determine whether the pacing pulses achieved local capture along the corresponding pacing vectors. At least one of the pacing pulses or pacing vectors are updated based on the comparison of the evoked responses to the template in order to determine a local capture threshold for the corresponding pacing vectors.

8 Claims, 6 Drawing Sheets

METHOD AND SYSTEM FOR VALIDATING LOCAL CAPTURE IN MULTISITE PACING DELIVERY

BACKGROUND

One or more embodiments of the inventive subject matter relate to validating local capture of pacing pulses in multisite pacing delivery.

Implantable stimulation devices or cardiac pacemakers are a class of cardiac rhythm management devices that provide electrical stimulation in the form of pacing pulses to selected chambers of the heart. As the term is used herein, a pacemaker is any cardiac rhythm management device with a pacing functionality regardless of any additional functions it may perform, such as cardioversion/defibrillation.

A pacemaker is comprised of two major components, a pulse generator and a lead. The pulse generator generates the pacing stimulation pulses and includes the electronic circuitry and the power cell or battery. The lead, or leads, is implanted within the heart and has electrodes which electrically couple the pacemaker to the desired heart chamber(s). A lead may provide both unipolar and bipolar pacing and/or sensing configurations. In the unipolar configuration, the pacing pulses are applied and responses are sensed between an electrode carried by the lead and a case of the pulse generator or a coil electrode of another lead within the heart. In the bipolar configuration, the pacing pulses are applied and responses are sensed between a pair of electrodes carried by the same lead. Pacemakers are also described as single-chamber or dual-chamber systems. A single-chamber system stimulates and senses in one chamber of the heart (an atrium or a ventricle). A dual-chamber system stimulates and/or senses in at least one atrial chamber and at least one ventricular chamber. Recently, there has been the introduction of pacing systems that stimulate multiple sites in the same chamber, termed multisite stimulation systems.

When the patient's own intrinsic rhythm fails, pacemakers can deliver pacing pulses to a heart chamber to induce a depolarization of that chamber, which is followed by a mechanical contraction of that chamber. Pacemakers further include sensing circuits that sense cardiac activity for the detection of intrinsic cardiac events such as intrinsic atrial depolarizations (detectable as P waves) and intrinsic ventricular depolarizations (detectable as R waves). By monitoring cardiac activity, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

In order for a pacemaker to control the heart rate in the manner described above, the pacing pulses delivered by the device must achieve "local capture," which refers to causing sufficient depolarization of the myocardium surrounding a particular pacing electrode such that a desired propagating wave of excitation and contraction result (i.e., a heartbeat). A pacing pulse that does not capture the heart is thus an ineffective pulse. An ineffective pulse not only wastes energy from the pacemaker, which has limited energy resources (e.g., a battery), but can have deleterious physiological effects as well. A number of factors can determine whether a given pacing pulse will achieve local capture, but the principal factor is the energy of the pulse. The pacing pulse energy (e.g., pacing output) is a function of current, voltage, and duration. The pacing output can be adjusted to modify pulse parameters such as pulse amplitude, pulse width, and/or pacing delay to achieve local capture along the corresponding pacing vectors in response to the adjusted pacing pulses.

The minimum pacing output necessary to achieve local capture by a particular pacing channel (e.g., pacing vector) is referred to as the "local capture threshold." The local capture threshold is not fixed, but rather, may increase and decrease during of the course of a single day, on a daily basis, and/or in response to changes in cardiac disease status. To reduce current drain on the limited power supply, it is desirable to automatically adjust the pacemaker such that the amount of stimulation energy delivered to the myocardium is maintained at a level that will reliably capture the heart without wasting power. Such a process is often referred to as "automatic capture verification and threshold search" or "autocapture," but may be referred to by other names.

Recent studies have suggested that bi-ventricular (BiV) pacing (e.g., delivering pacing stimulus between the left ventricle and the right ventricle) from at least two left ventricular (LV) sites can improve clinical outcome in patients undergoing cardiac resynchronization therapy (CRT). The improved clinical outcome is likely due to improved hemodynamic response that can be achieved using multi-site LV pacing, in comparison with conventional single site BiV pacing. Pacing at more than one site within the LV chamber is referred to as multisite left ventricular (MSLV) pacing. To provide such MSLV pacing, leads have been developed that include multiple electrodes for placement in the LV chamber. For example, St. Jude Medical Inc. (headquartered in St. Paul, Minn.) has developed the Quartet™ left ventricular pacing lead, which includes four pacing electrodes on the left ventricular lead—enabling up to 10 pacing configurations (e.g., pacing vectors). One goal of MSLV pacing is to cause local capture at each LV pacing site (e.g., along each pacing vector), so the resulting depolarization waveforms propagate throughout the LV chamber in a desired manner. Another goal of MSLV pacing is to deliver pacing pulses that have pacing energy outputs that slightly exceed the local capture thresholds to conserve the limited energy available from the battery of the pacemaker.

One challenge associated with MSLV pacing relates to detecting achievement of local capture and the failure to achieve local capture (e.g., lack or loss of local capture) along each pacing vector when multiple sites are being paced within the LV chamber. Local capture thresholds vary with different pacing vectors and locations. Therefore, as expected, local capture thresholds vary more dramatically with quadripolar LV leads (e.g., such as the Quartet™ lead) than bipolar or unipolar LV pacing leads. Local capture thresholds for each pacing vector also vary on an individual patient-by-patient basis, and even fluctuate within a single patient, as mentioned above. Therefore, each of the selected pacing vectors may have a different local capture threshold. One pacing pulse delivered at a given pacing output may achieve local capture if delivered along a first vector, but not if delivered along a second vector. There is a need to distinguish between local capture along one pacing vector and local capture along another pacing vector.

To detect whether a pacing pulse achieved local capture in surrounding tissue along a pacing vector, a sensing vector is used to monitor for an "evoked response" associated with a corresponding pacing vector following the pacing pulse. The evoked response is a depolarization waveform that results from the pacing pulse and evidences contraction of the paced chamber generally along the pacing vector. Another challenge associated with MSLV pacing relates to accurately monitoring evoked responses specific to individual pacing vectors, especially when the pacing pulses are delivered simultaneously or in close succession. For example, pacing at one LV site can result in pacing artifacts at a second LV site, which interferes with the sensed evoked response at the second LV site.

Although capture verification may be performed in a clinical setting by a clinician, the pacemaker itself may verify capture using an autocapture algorithm that is configured to detect lack of local capture and adjust pacing parameters automatically. Autocapture algorithms have been developed, but such algorithms have typically been designed for only one or two pacing pulses being delivered in a same cardiac chamber per cardiac cycle. Accordingly, such algorithms may not effectively control more than two pacing pulses being delivered within the same cardiac chamber per cardiac cycle. In addition to the challenges already discussed, it is also noted that providing additional pacing pulses (e.g., three or more pulses) per cardiac cycle increases the drain on the battery. Accordingly, it is important to improve energy efficiency such that the pacing pulses are delivered with respective pacing outputs that reliably achieve local capture but do not waste the limited energy available.

SUMMARY

In an embodiment, a method is provided for use with an implantable system including a lead having multiple electrodes implantable proximate to a patient's LV chamber. The method includes simultaneously delivering pacing pulses over corresponding pacing vectors. The pacing vectors are defined by electrodes proximate to the LV chamber. The method includes recording evoked responses that are responsive to the pacing pulses. The evoked responses are associated with the corresponding pacing pulses and measured over separate corresponding sensing channels. The method also includes comparing the evoked responses to at least one template. The template represents local capture of a local LV tissue region along one or more of the corresponding pacing vectors. The comparison is used to determine whether the pacing pulses achieved local capture along the corresponding pacing vectors. The method further includes updating at least one of the pacing pulses or pacing vectors based on the comparison of the evoked responses to the at least one template in order to determine a local capture threshold for the corresponding pacing vectors.

In an embodiment, an implantable cardiac stimulation (ICS) system is provided including a lead having multiple electrodes implantable proximate to a patient's LV chamber. The ICS system includes a pacing pulse delivery (PPD) module configured to simultaneously deliver pacing pulses over corresponding pacing vectors. The pacing vectors are defined by electrodes proximate to the LV chamber. The ICS system includes an evoked response recording (ERR) module configured to record evoked responses that are responsive to the pacing pulses. The evoked responses are associated with the corresponding pacing pulses and measured over separate corresponding sensing channels. The ICS system also includes an evoked response comparison (ERC) module configured to compare the evoked responses to at least one template. The at least one template represents local capture of a local LV tissue region along one or more of the corresponding pacing vectors. The comparison is used to determine whether the pacing pulses achieved local capture along the corresponding pacing vectors. The ICS system further includes a pacing pulse update (PPU) module configured to update at least one of the pacing pulses or the pacing vectors based on the comparison of the evoked responses to the at least one template in order to determine a local capture threshold for the corresponding pacing vectors.

DETAILED DESCRIPTION

Figure 1:
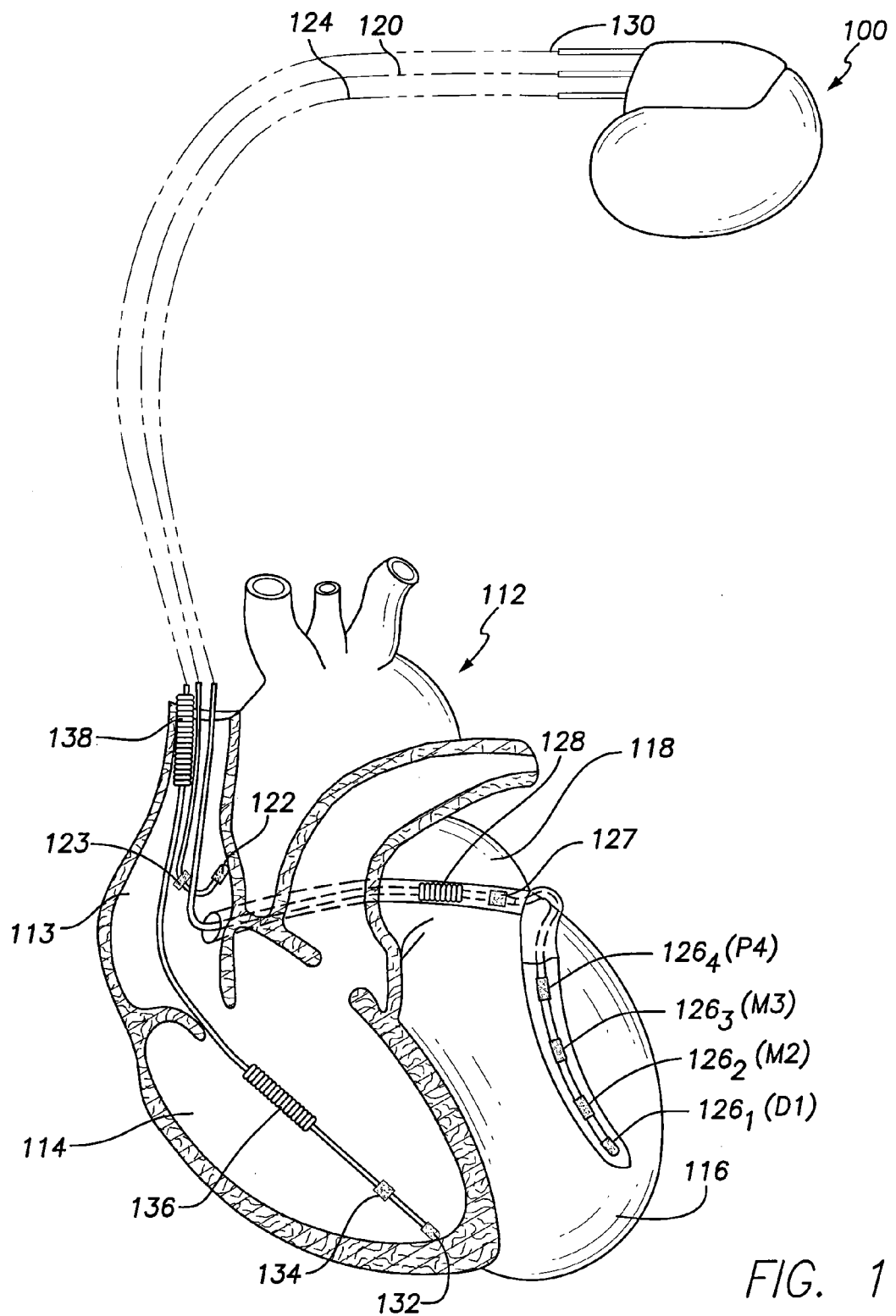
FIG. 1 illustrates an implantable stimulation device implanted into a patient's heart according to an embodiment.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor or a block or random access memory, hard disk, or the like). Similarly, the programs may be standalone programs, may be incorporated as subroutines in an operating system, may be functions in an installed imaging software package, and the like. It should be understood that the various embodiments are not limited to the arrangements and instrumentality shown in the drawings.

One or more embodiments generally relate to chronically implantable cardiac stimulation (ICS) devices and systems such as pacemakers and implantable cardioverter-defibrillators (ICDs). One or more embodiments relate, in particular, to such devices and systems that are capable of multi-site left ventricular (MSLV) pacing, and methods for use therewith. Some of the embodiments relate to an automatic capture verification and threshold search algorithm for use with MSLV pacing. In view of the above, FIGS. 1 and 2 illustrate an ICS system capable of delivering MSLV pacing, in which embodiments described herein may be implemented.

Figure 2:
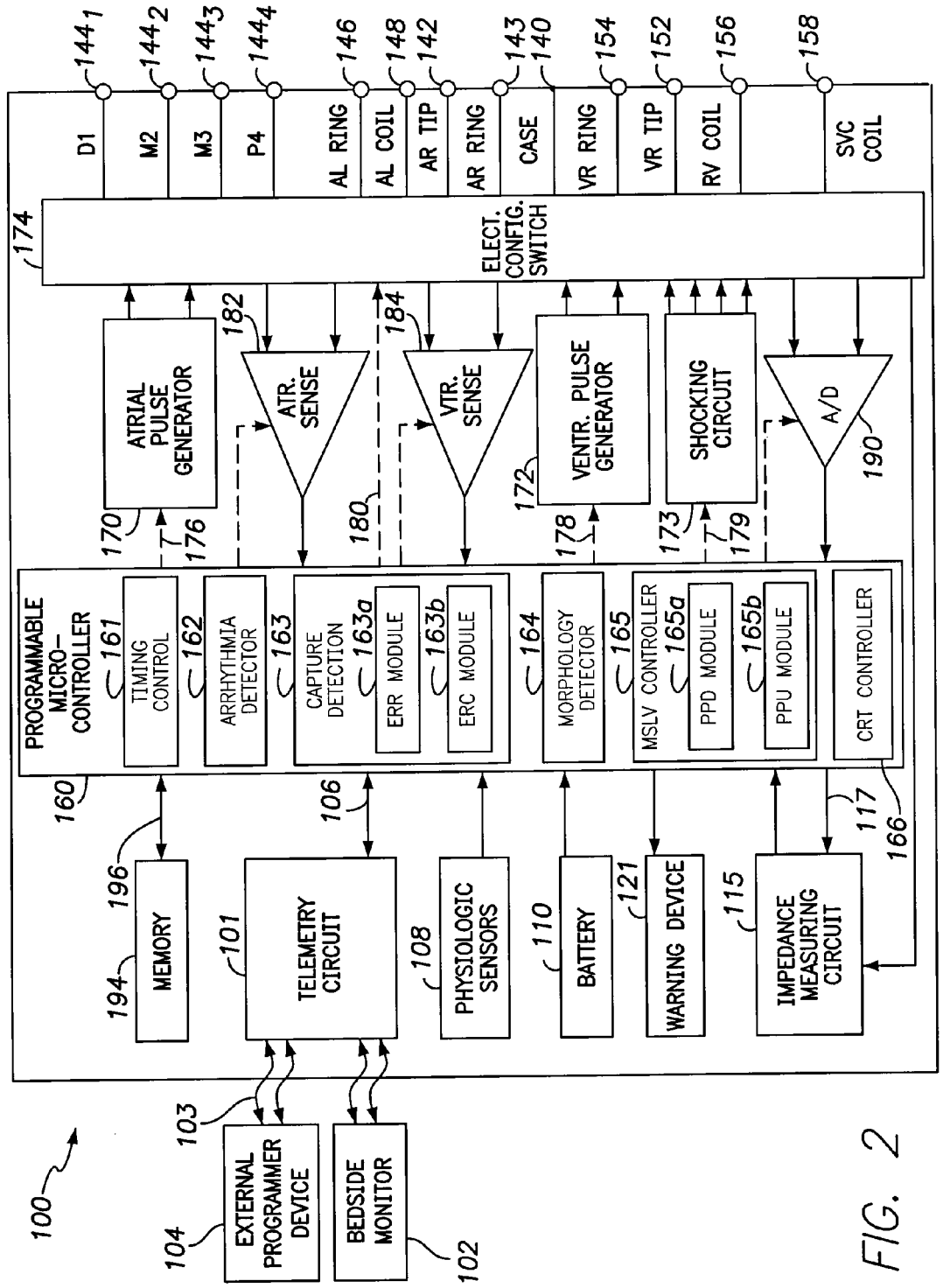
FIG. 2 illustrates a block diagram of internal components of the implantable stimulation device of FIG. 1 according to an embodiment.

FIG. 1 illustrates an implantable cardiac stimulation system 100 in electrical communication with multiple leads implanted into a patient's heart 112 for delivering multi-chamber stimulation and sensing cardiac activity according to an embodiment. The ICS system 100 may be a dual-chamber stimulation device, including a pacemaker/ICD, capable of treating both fast and slow arrhythmias with stimulation therapy, including cardioversion, defibrillation, and pacing stimulation, including MSLV pacing. The ICS system 100 may be referred to herein as pacemaker/ICD 100. To provide atrial chamber pacing stimulation and sensing, pacemaker/ICD 100 is shown in electrical communication with a heart 112 by way of a left atrial (LA) lead 120 having an atrial tip electrode 122 and an atrial ring electrode 123 implanted in the atrial appendage 113. Pacemaker/ICD 100 is also in electrical communication with the heart 112 by way of a right ventricular (RV) lead 130 having, in this embodiment, a ventricular tip electrode 132, an RV ring electrode 134, an RV coil electrode 136, and a superior vena cava (SVC) coil electrode 138. Typically, the RV lead 130 is transvenously inserted into the heart 112 so as to place the RV coil electrode 136 in the RV apex, and the SVC coil electrode 138 in the superior vena cava. Accordingly, the RV lead 130 is capable of receiving cardiac signals and delivering stimulation in the form of pacing and shock therapy to the right ventricle 114 (also referred to as the RV chamber).

To sense left atrial and ventricular cardiac signals and to provide left ventricle 116 (e.g., left chamber) pacing therapy, pacemaker/ICD 100 is coupled to a multi-pole LV lead 124 designed for placement in the "CS region." As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the CS. In an embodiment, an LV lead 124 is designed to receive atrial and ventricular cardiac signals and to deliver left ventricular pacing therapy using a set of four LV electrodes 126 that includes electrodes $126_1$, $126_2$, $126_3$, and $126_4$ (thereby providing a quadripolar lead). The LV lead 124 also may deliver left atrial pacing therapy using at least an LA ring electrode 127 and shocking therapy using at least an LA coil electrode 128. In alternate embodiments, the LV lead 124 includes the LV electrodes $126_1$, $126_2$, $126_3$, and $126_4$, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead—enabling up to 10 pacing configurations (e.g., pacing vectors).

The LV electrode $126_1$ is shown as being the most "distal" LV electrode with reference to how far the electrode is from the left atrium 118. The LV electrode $126_4$ is shown as being the most "proximal" LV electrode 126 to the left atrium 118. The LV electrodes $126_2$ and $126_3$ are shown as being "middle" LV electrodes, between the distal and proximal LV electrodes $126_1$ and $126_4$, respectively. Accordingly, so as to more aptly describe their relative locations, the LV electrodes $126_1$, $126_2$, $126_3$, and $126_4$ may be referred to respectively as electrodes D1, M2, M3, and P4 (where "D" stands for "distal", "M" stands for "medial" or "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The four LV electrodes 126 are configured such that each electrode may be utilized to deliver pacing pulses and/or sense pacing pulses (e.g., monitor the response of the LV tissue to a pacing pulse). Thus, each LV electrode 126 may be controlled to function as a cathode or an anode. Pacing pulses may be directionally provided between at least two electrodes to define a pacing vector. The electrodes that define the pacing vectors may be electrodes in the heart 112 or located externally to the heart 112 (e.g., on a housing/case device). The LV electrodes 126 may be used to provide various different pacing vectors. Some of the vectors are intraventricular LV vectors (e.g., vectors between two of the LV electrodes 126), while other vectors are interventricular vectors (e.g. vectors between an LV electrode 126 and the RV coil 136 or another electrode remote from the left ventricle 116). Below is a list of exemplary vectors that may be used for pacing and/or sensing using the LV electrodes D1, M2, M3, and P4 and the RV coil 136. In the following list, the electrode to the left of the arrow is assumed to be the cathode, and the electrode to the right of the arrow is assumed to be the anode.

D1→RV coil
M2→RV coil
M3→RV coil
P4→RV coil
D1→M2
D1→P4
M2→P4
M3→M2
M3→P4
P4→M2

Although three leads 120, 124, and 130 are shown in FIG. 1, fewer or additional leads with various numbers of pacing, sensing, and/or shocking electrodes may optionally be used. For example, the RV lead 124 may have more or less than four LV electrodes 126.

FIG. 2 illustrates a simplified block diagram of internal components of the ICS system 100 (e.g., pacemaker/ICD) according to an embodiment. While a particular pacemaker/ICD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and/or pacing stimulation. A housing 140 for pacemaker/ICD 100, shown schematically in FIG. 2, is often referred to as the "CAN," "case," or "case electrode," and may be programmably selected to act as the anode for at least some unipolar modes. The housing 140 may further be used as a return electrode alone or in combination with one or more of the coil electrodes 128, 136 and 138 (all shown in FIG. 1) for shocking purposes.

The ICS system 100 further includes a connector (not shown) having a plurality of terminals, 142, 143, $144_1$-$144_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal ($A_R$ TIP) 142 adapted for connection to the atrial tip electrode 122 (shown in FIG. 1) and an RA ring ($A_R$ RING) electrode 143 adapted for connection to the RA ring electrode 123 (shown in FIG. 1). To achieve left chamber sensing, pacing, and shocking, the connector includes an LV tip terminal $144_1$ adapted for connection to the D1 electrode and additional LV electrode terminals $144_2$, $144_3$, and $144_4$ adapted for connection to the M2, M3, and P4 electrodes, respectively, of the quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV shocking terminal (RV COIL) 156, and an SVC shocking terminal (SVC COIL) 158, which are adapted for connection to the RV tip electrode 132, the RV ring electrode 134, the RV coil electrode 136, and the SVC coil electrode 138 (all four shown in FIG. 1), respectively.

At the core of the ICS system 100 is a programmable microcontroller 160, which controls the various modes of stimulation therapy. As is well known in the art, the microcontroller 160 (also referred to herein as a control unit or controller) typically includes a microprocessor, or equivalent control circuitry, designed specifically for controlling the delivery of stimulation therapy. The microcontroller 160 may further include RAM or ROM memory, logic and timing circuitry, state machine circuitry, and I/O circuitry. Typically, the microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. The use of microprocessor-based control circuits for performing timing and data analysis functions are well known in the art.

An atrial pulse generator 170 and a ventricular pulse generator 172 generate pacing stimulation pulses for delivery by the RA lead 120, the RV lead 130, and/or the LV lead 124 (all three leads shown in FIG. 1). The pacing pulses are routed from the pulse generators 170, 172 to selected electrodes within the leads 120, 124, 130 through an electrode configuration switch 174. It is understood that in order to provide stimulation therapy in each of the four chambers of the heart, the atrial and ventricular pulse generators 170 and 172, may include dedicated, independent pulse generators, multiplexed pulse generators, or shared pulse generators. The pulse generators 170, 172 are controlled by the microcontroller 160 via appropriate control signals 176 and 178, respectively, to trigger or inhibit the stimulation pulses.

The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, determines the polarity of the stimulation pulses (e.g., unipolar, bipolar, combipolar, etc.) by selectively actuating the appropriate combination of switches (not shown) as is known in the art. The switch 174 also switches among the various LV electrodes 126 to select the channels to deliver and/or sense one or more of the pacing pulses.

Atrial sensing circuits 182 and ventricular sensing circuits 184 may also be selectively coupled to the RA lead 120, LV lead 124, and/or the RV lead 130 (all three leads shown in FIG. 1) through the switch 174 for detecting the presence of cardiac activity in each of the four chambers of the heart. Accordingly, the atrial sensing circuits 182 and ventricular sensing circuits 184 may include dedicated sense amplifiers, multiplexed amplifiers, or shared amplifiers. The switch 174 determines the "sensing polarity" of the cardiac signal by selectively opening and/or closing the appropriate switches, as is also known in the art. In this way, a clinician may program the sensing polarity independent of the stimulation polarity. The outputs of the atrial and ventricular sensing circuits 182 and 184 are connected to the microcontroller 160. The outputs, in turn, are able to trigger or inhibit the atrial and ventricular pulse generators 170 and 172, respectively, in a demand fashion in response to the absence or presence of cardiac activity in the appropriate chambers of the heart 112 (shown in FIG. 1).

Cardiac signals are also applied to the inputs of an analog-to-digital (A/D) data acquisition system 190. The A/D data acquisition system 190 is configured to acquire intracardiac electrogram (IEGM) signals, convert the raw analog data into a digital signal, and store the digital signals for later processing and/or telemetric transmission. The telemetric transmission may be to an external programmer 104, a bedside monitor 102, and/or a personal advisory module (PAM). The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control circuitry 161 to control the timing of the stimulation pacing pulses, including, but not limited to, pacing rate, atrio-ventricular delay, interatrial conduction delay, interventricular conduction delay, and/or intraventricular delay. The timing control circuitry 161 can also keep track of the timing of refractory periods, blanking intervals, noise detection windows, evoked response detection windows, alert intervals, marker channel timing, etc., which is well known in the art.

The microcontroller 160 further includes an arrhythmia detector 162 for operating the system 100 as an implantable cardioverter/defibrillator device. The detector 162 determines desirable times to administer various therapies. For example, the detector 162 may detect the occurrence of an arrhythmia and automatically control the application of an appropriate electrical shock therapy to the heart aimed at terminating the detected arrhythmia. To this end, the microcontroller 160 further controls a shocking circuit 173 by way of a control signal 179. The shocking circuit 173 generates shocking pulses that are applied to the heart of the patient through at least two shocking electrodes. The shocking pulses may be selected from the LA coil electrode 128, the RV coil electrode 136, and/or the SVC coil electrode 138 (all three electrodes shown in FIG. 1). The housing/case 140 may act as an active electrode in combination with the RV electrode 136, or as part of a split electrical vector using the SVC coil electrode 138 or the LA coil electrode 128 (e.g., with the RV electrode as a common electrode).

The microcontroller 160 may additionally include a morphology detector 164 and a CRT controller 166. The CRT controller 166 controls cardiac resynchronization therapy, which can be performed in conjunction with MSLV pacing. The arrhythmia detector 162, morphology detector 164, and/or CRT controller 166 may be implemented in hardware as part of the microcontroller 160, or as software/firmware instructions programmed into the system 100 and executed on the microcontroller 160 during certain modes of operation.

An MSLV controller 165 within the microcontroller 160 controls the actual delivery of MSLV pacing pulses. The MSLV controller 165 controls the number, timing, and output of the pacing pulses delivered during each cardiac cycle, as well as over which pacing vectors the pacing pulses are to be delivered. The MSLV controller 165 also selects the sensing channels over which the responses to the pulses are detected. The sensing channels or vectors are associated with corresponding pacing vectors. As an example, the MSLV controller 165 may control the ventricular pulse generator 172 to simultaneously deliver four pacing pulses over corresponding pacing vectors P4-RVC, M3-RVC, M2-RVC, and D1-RVC defined by the LV electrodes 126 and the RV coil 136 (both shown in FIG. 1). Immediately after pacing, the electrodes that define the selected sensing channels monitor the LV tissue for an evoked response. Optionally, the sensing channels may be selected as the same vectors as the corresponding pacing vectors. The MSLV controller 165 may include a pacing pulse delivery (PPD) module 165a that is configured to select the pacing and sensing vectors and deliver the pacing pulses. The MSLV controller 165 also may include a pacing pulse update (PPU) module 165b configured to update the pacing parameters between cardiac pulse cycles. For example, based on communication with other modules in the microcontroller 160, the PPU module 165b may adjust the pacing pulses and/or the pacing vectors for a subsequent cardiac cycle.

The microcontroller 160 further includes a local capture detection module 163. The local capture detection module 163, as described herein, may aid in acquisition, analysis, etc., of data streams relating to evoked responses associated with the corresponding pacing pulses and measured over separate corresponding sensing channels. In particular, the capture detection module 163 may act to distinguish local capture versus non-capture versus undesired fusion. The capture detection module 163 may include an evoked response recording (ERR) module 163a configured to record data streams relating to the evoked responses that are responsive to the pacing pulses. The capture detection module 163 may also include an evoked response comparison (ERC) module 163b configured to compare the recorded data streams to at least one template that represents local capture of a local LV tissue region along one of the corresponding pacing vectors. The capture detection module 163 may communicate with the MSLV controller 165 to control the automatic capture verification and threshold search algorithm of one or more embodiments herein.

For example, in an embodiment, after the PPD module 165a controls the delivery of a set of pacing pulses along corresponding pacing vectors during a cardiac cycle, the ERR module 163a records the evoked responses associated with the corresponding pacing pulses. The evoked responses may be sensed over the sensing channels selected by the PPD module 165a. The evoked responses may be collected by the ERR module 163a as intracardiac electrograms (IEGMs) that are specific to the corresponding pacing vectors. The ERR module 163a may at least temporarily store the evoked responses within the microcontroller 160 or within a memory 194 of the ICS system 100. Optionally, the ERR module 163a may store the evoked response data within a memory of an external device (e.g., external programmer device 104, bedside monitor 102, and the like) by communicating the evoked response data using a telemetry circuit 101.

As further discussed below, the ERC module 163b may then compare the recorded data relating to the evoked responses to at least one evoked response template (e.g., ER template). The ER template(s) represents local capture of a local LV tissue region along one or more of the corresponding pacing vectors. The ERC module 163b compares the evokes responses to the ER template(s) to determine whether one or more of the pacing pulses achieved local capture along the corresponding pacing vectors. For comparison purposes, the ER template may be accessed by the ERC module 163b from another module within the microcontroller 160, from the memory 194, and/or from an external device. For example, at least one ER template may be uploaded from a clinician's computer at the clinician's office to the memory 194 of the ICS system 100, from which the at least one ER template is accessed by the ERC module 163b.

Both the MSLV controller 165 and the local capture detection module 163 may be used to implement various algorithms and/or methods presented below. For example, as discussed above, the MSLV controller 165 (e.g., via the PPD module 165a) determines the parameters (e.g., number of pulses, pulse output, pulse duration, timing between pulses, pacing vectors, sensing vectors, and the like). The local capture detector module 163 (e.g., via the ERR module 163a and the ERC module 163b) assists in the recording of the evoked responses and compares the evoked responses to the ER template(s) to determine if one or more of the pacing pulses achieved local capture. Subsequently, the information determined by the ERC module 163b from comparing the evoked responses to the ER template(s) is used by the PPU module 165b to update the pacing parameters in an upcoming cardiac cycle. For example, based on the comparison of the evoked responses to the ER template(s), the PPU module 165b is configured to update at least one of the pacing pulses of the pacing vectors in order to zero in on a local capture threshold for a corresponding pacing vector. Therefore, in an embodiment, the MSLV controller 165 and the local capture detector module 163 within the microcontroller 160 work together to implement the various algorithms and/or methods presented herein.

Depending upon the implementation, the aforementioned components of the microcontroller 160 may be implemented in hardware as part of the microcontroller 160, or as software/firmware instructions programmed into the device and executed on the microcontroller 160 during certain modes of operation. In addition, the modules may be separate software modules or combined to permit a single module to perform multiple functions. For example, the MSLV controller 165 and the local capture detector module 163 may be combined into one module. In addition, although shown as being components of the microcontroller 160, some or all of the components/modules described above may be implemented separately from the microcontroller 160 using application specific integrated circuits (ASICs) or the like.

The microcontroller 160 is further coupled to a memory 194 by a suitable data/address bus 196. The programmable operating parameters used by the microcontroller 160 are stored in the memory 194 and modified, as required, in order to customize the operation of pacemaker/ICD 100 to suit the needs of a particular patient. Such operating parameters define, for example, the amplitude or magnitude of the pacing pulses, wave shape, pulse duration, and/or vector (e.g., including electrode polarity) for the pacing pulses. Other pacing parameters may include base rate, rest rate, and/or circadian base rate. The memory 194 also may be utilized by the local capture detection module 163 to store, at least temporarily, recorded evoked responses that are to be compared to the one or more templates to determine whether the pacing pulses achieved local capture along the corresponding pacing vectors.

Advantageously, the operating parameters of the implantable pacemaker/ICD 100 may be non-invasively programmed into the memory 194 through a telemetry circuit 101 in telemetric communication with an external programmer device 104 or a bedside monitor 102, such as a programmer, transtelephonic transceiver or a diagnostic system analyzer. The telemetry circuit 101 is activated by the microcontroller 160 through a control signal 106. The telemetry circuit 101 advantageously allows IEGMs and status information relating to the operation of pacemaker/ICD 100 (contained in the microcontroller 160 or the memory 194) to be sent to the external device 102 through an established communication link 103. An internal warning device 121 may be provided for generating perceptible warning signals to a patient and/or caregiver via vibration, voltage, or other methods.

Pacemaker/ICD 100 further includes an accelerometer or other physiologic sensor 108. The physiologic sensor 108 is commonly referred to as a "rate-responsive" sensor because it is typically used to adjust the pacing stimulation rate according to the exercise state (e.g., heart rate) of the patient. However, the physiological sensor 108 may further be used to detect changes in cardiac output, changes in the physiological condition of the heart, and/or diurnal changes in activity (e.g., detecting sleep and wake states and arousal from sleep). Accordingly, the microcontroller 160 may respond to such changes by adjusting the various pacing parameters (such as rate, interatrial delay, interventricular delay, etc.) at which the atrial and ventricular pulse generators 170 and 172 generate stimulation pulses. While shown as being included within pacemaker/ICD 100, it is to be understood that the physiologic sensor 108 may also be external to the pacemaker/ICD 100. Optionally, the physiologic sensor 108 may still be implanted within or carried by the patient. A common type of rate responsive sensor 108 is an activity sensor incorporating an accelerometer or a piezoelectric crystal, which is mounted within the housing/case 140 of pacemaker/ICD 100. Other types of physiologic sensors 108 are also known, such as sensors that sense the oxygen content of blood, respiration rate and/or minute ventilation, pH of blood, ventricular gradient, stroke volume, cardiac output, contractility, and the like.

The pacemaker/ICD 100 additionally includes a battery 110, which provides operating power to all of the circuits shown in FIG. 2. The makeup of the battery 110 may vary depending on the capabilities of pacemaker/ICD 100. If the system only provides low voltage therapy (e.g., for repetitive pacing pulses), a lithium iodine or lithium copper fluoride cell typically may be utilized. For a pacemaker/ICD that employs shocking therapy, the battery may be configured to be capable of operating at low current drains for long periods and then providing high-current pulses (for capacitor charging) when the patient requires a shock pulse. The battery 110 may also be configured to have a predictable discharge characteristic so that elective replacement time can be detected. As an alternative to a single battery, the pacemaker/ICD 100 may include multiple batteries depending on the power requirements and available space within the pacemaker/ICD 100.

As further shown in FIG. 2, the pacemaker/ICD 100 has an impedance measuring circuit 112, which is enabled by the microcontroller 160 via a control signal 114. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is advantageously coupled to the switch 174 so that any desired electrode may be used.

The above described implantable cardiac stimulation system 100 was described as an exemplary pacemaker/ICD. One of ordinary skill in the art would understand that one or more embodiments herein may be used with alternative types of implantable devices. Accordingly, embodiments should not be limited to using only the above described device 100.

Figure 3:
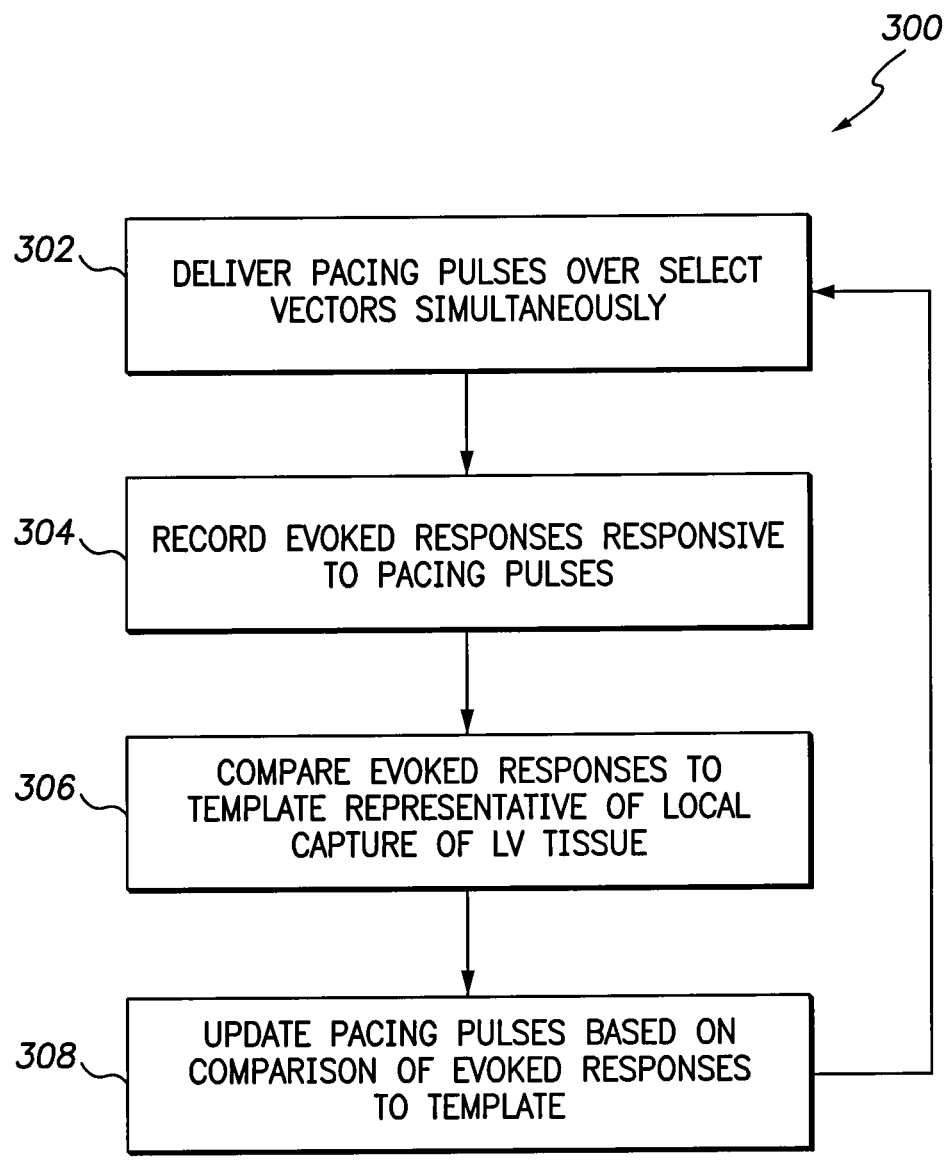
FIG. 3 is a flow chart for a method of simultaneous multi-site local capture according to an embodiment.

FIG. 3 is a flow chart for a method 300 of simultaneous multisite local capture according to an embodiment. The method 300 may be performed using an implantable device, such as the ICS system 100 shown in FIGS. 1 and 2. The implantable device has a lead with multiple electrodes, such as the quadripolar LV lead 124 (shown in FIG. 1). The method 300 is described with reference to the ICS system 100 of FIGS. 1 and 2, although other devices may be used instead of or in addition to the ICS system 100. The operations of the method 300 described below may be implemented in an autocapture algorithm that controls an implantable device to automatically determine local capture thresholds of several electrode pacing vectors simultaneously.

At 302, multiple pacing pulses are simultaneously delivered over corresponding select multiple pacing vectors. The pacing vectors are at least partially defined by the LV electrodes 126 within the LV chamber 116. The pacing vectors may be selected by the MSLV controller 165 within the microcontroller 160. For example, the MSLV controller 165 may control the electrode configuration switch 174 to make electrical contact with the appropriate terminals associated with the electrodes. The pacing pulses may be delivered by the MSLV controller 165 sending control signals 178 to the ventricular pulse generator 172. The ventricular pulse generator 172 responds to the signals by transmitting an electrical output to one or both electrodes that define a select pacing vector. The electrical output(s) create an electrical potential difference between the electrodes defining a vector, inducing a depolarization wave in the surrounding LV tissue region.

In an embodiment, the RV coil 136 may be selected as the common anode for each of the pacing vectors. A pacing pulse may be delivered from electrode D1 to the RV coil 136 along a pacing vector D1-RVC. The depolarization wave propagates from electrode D1 generally toward the RV coil 136. Similarly, other LV pacing electrodes 126 on the LV lead 124 may be used to pace, such as along vectors M2-RVC, M3-RVC, and P4-RVC. In an embodiment, a separate pacing pulse is delivered over two or more of the vectors D1-RVC, M2-RVC, M3-RVC, and P4-RVC substantially at the same time. In other embodiments, pacing pulses may be delivered over pacing vectors defined between two LV electrodes 126. For example, intraventricular vectors, such as D1-M2, D1-P4, M2-P4, M3-M2, M3-P4, and P4-M2, may be created along the quadripolar LV lead 124. In the present example, up to ten selectable pacing vectors may be used.

In addition to selecting the pacing vectors, the MSLV controller 165 may control the parameters that define the pacing pulses, such as the timing between pulses, amplitude (e.g., voltage), and pulse duration. For example, the MSLV controller 165 may control the ventricular pulse generator 172 to deliver simultaneous pacing pulses along corresponding select pacing vectors at a controlled rate. In an embodiment, each of the pacing pulses has the same pacing output (e.g., voltage). In other embodiments, the pacing pulses over the different vectors may have different pacing outputs and/or may not be delivered simultaneously with other pulses.

At 304, after the pacing pulses are delivered, the microcontroller 160 switches to a sensing state to sense or listen for, and record, evoked responses that are responsive to the pacing pulses. The evoked response represents a wave of depolarization that propagates through the LV tissue as a result of a corresponding pacing pulse. The evoked response for each corresponding pacing pulse is sensed by an electrode combination that includes at least the LV electrode used to deliver the corresponding pacing pulse. For example, in the embodiment where the RV coil 136 is the common anode for all paced vectors, the individual sensing vectors may also be defined between the RV coil 136 and the corresponding LV electrodes. Optionally, the sensing vectors may be defined by different electrodes than the pacing vectors. For example, a pulse may be delivered along pacing vector D1-RVC, but the evoked response in response to the pulse may be sensed along sensing vector D1-CAN, where CAN represents an electrode on the housing/case 140. Each sensing vector represents a sensing channel.

The evoked response may be sensed by determining an electrical potential difference between the electrodes in a sensing channel. For example, sensed electrical activity (e.g., voltage and/or current) at each electrode may be routed through the electrode configuration switch 174 to the ventricular sensing circuit 184, which includes an amplifier. The ventricular sensing circuit 184 may compare the electrical activity sensed to determine the electrical potential difference between the electrodes at various times. From the ventricular sensing circuit 184, one or more data signals may be sent to the capture detection module 163 for recordation and analysis of the data.

The evoked responses are recorded as separate data streams measured over the separate corresponding sensing channels over time. The data streams representative of the evoked responses may be recorded by the ERR module 163*a*. The data streams may be stored internally in the memory 194 of the implantable device 100 and/or transmitted to an external device for processing and/or storage. For example, the data stream may include the sensed electrical potential difference along the corresponding sensing channel over time, such as an IEGM. The data streams may also be stored with timing information, vector identification, pacing pulse information, and the like.

At 306, the evoked responses are compared to one or more templates that are representative of expected evoked response signatures associated with local capture of the surrounding LV tissue. The surrounding LV tissue is the tissue along the corresponding pacing vectors. Each of the evoked responses is compared to an evoked response template (e.g., ER template) to determine whether the associated pacing pulses achieved local capture. The comparison and local capture determination may be controlled by the ERC module 163*b*.

Figure 4:
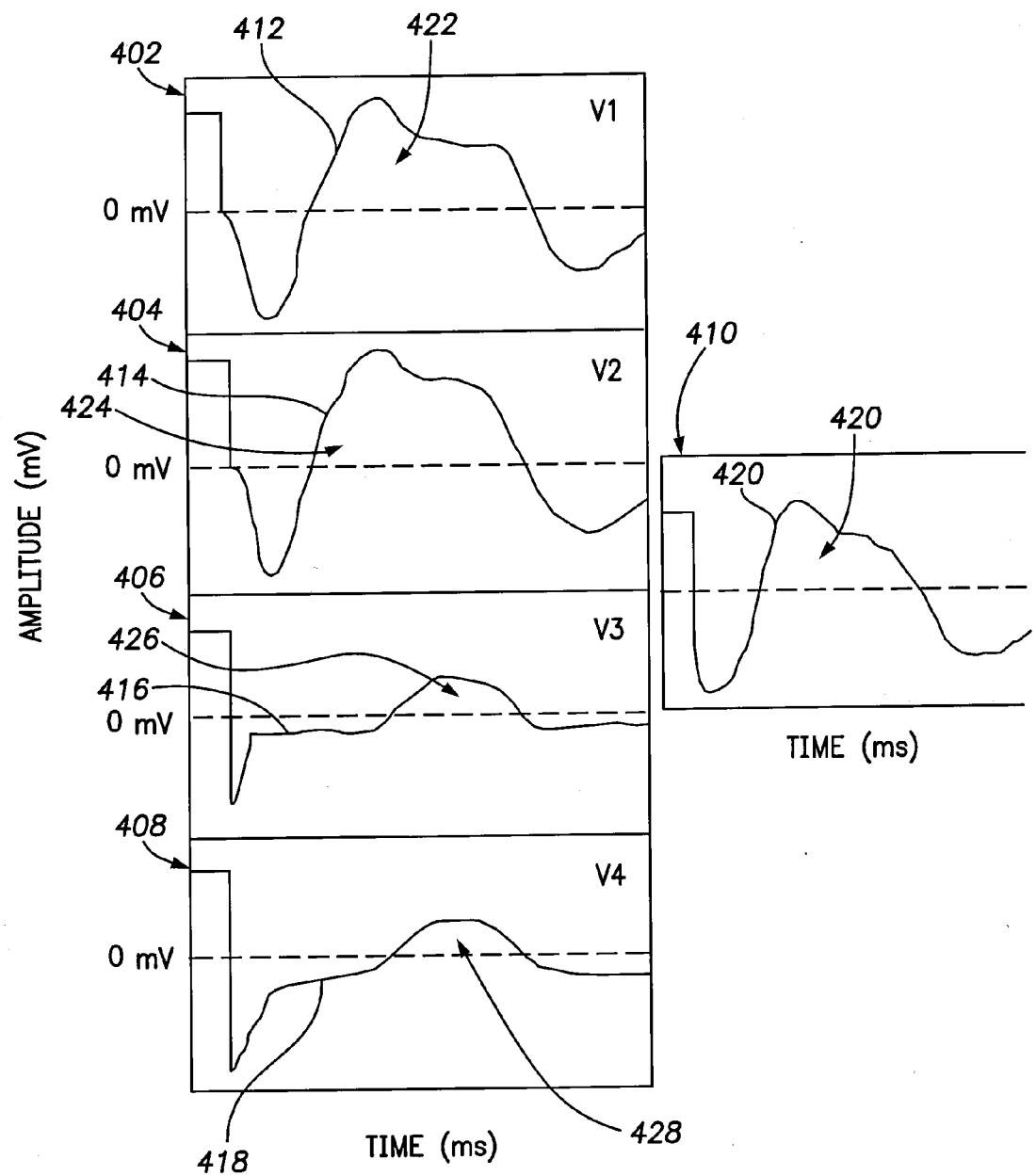
FIG. 4 displays example evoked responses that may be sensed following pacing pulses and an evoked response template in accordance with an embodiment.

FIG. 4 displays example graphs 402, 404, 406, and 408 of recorded data streams in connection with corresponding evoked responses that may be sensed following pacing pulses, and also shows an ER template 410 in accordance with an embodiment. The ER template 410 is shown side by side with the set of evoked response graphs 402-408 for comparison purposes. As an example, the graphs 402-410 are displayed as IEGM graphs plotting a sensed amplitude (in mV) over time (in ms). The evoked response graphs 402-408 are data streams measured in response to a set of simultaneous pacing pulses delivered along corresponding pacing vectors V1-V4, where graph 402 corresponds to V1, graph 404 corresponds to V2, graph 406 corresponds to V3, and graph 408 corresponds to V4. For example, V1 may be vector D1-RVC, V2 may be vector M2-RVC, V3 may be vector M3-RVC, and V4 may be vector P4-RVC. Optionally, V1-V4 may represent other pacing vectors defined at least partially by one or more of the LV electrodes D1, M2, M3, and P4.

The ER template 410 is representative of a known or expected evoked response that is indicative of successful local capture. In an example, the determination may be made by a clinician that is able to verify that the pacing pulse that caused the evoked response successfully achieved local capture of the surrounding LV tissue. The ER template 410 may be patient specific as capture thresholds and measured electrical potential along a propagating response wave vary from patient to patient. For example, the ER template 410 may be recorded after a pacing pulse is delivered to the patient in the presence of the clinician who determines whether local capture was successful. If the evoked response to the pacing pulse was determined to achieve local capture, the clinician may designate the evoked response as an ER template 410. The ER template 410 may be used as a threshold criteria basis to compare latter pacing pulses delivered to the same patient to determine if the subsequent pacing pulses also achieve local capture. By comparing plotted evoked responses 402-408 to an ER template 410, it can be determined whether one or more of the pacing pulses associated with the plotted evoked responses 402-408 also achieved local capture without requiring the clinician's further involvement. Once one or more ER templates 410 are designated, the ERC module 163*b* may be configured to automatically compare the data plotted in the evoked response graphs 402-408 to the ER template(s) 410 to determine which of the evoked responses, if any, have achieved local capture.

In an embodiment, the evoked response graphs 402-408 may be compared to a common ER template 410. Although capture thresholds and evoked responses vary among different pacing vectors and locations from patient to patient, an evoked response that achieves local capture may have certain universal characteristics. For example, although the individual vectors V1-V4 may yield different evoked response graphs 402-408 and exhibit different capture thresholds, the evoked response from each vector V1-V4 when local capture is achieved may have specific characteristics in common with the ER template 410. For example, some specific characteristics include the morphology of the sensed waveforms, the areas under the curves, etc., as discussed further in connection with FIG. 5.

In an alternative embodiment not shown in FIG. 4, each evoked response graph 402-408 may be compared to a separate unique ER template that is specific to the corresponding pacing vector V1, V2, V3, or V4. For example, an ER template for each of the vectors V1-V4 may be determined individually, such as by a clinician. Due to the differences in vectors and electrode positions, the recorded IEGM of one vector may differ from the recorded IEGM of a different vector even if both pacing pulses over the respective vectors achieved local capture. Therefore, each evoked response graph 402-408 may be compared to ER templates that are vector-specific to determine if the pacing pulses delivered over the corresponding vectors achieved local capture. For example, the plotted evoked response 402 over vector V1 may be compared to an IEGM that is determined to represent a waveform of an evoked response over vector V1 that has achieved local capture. The IEGM to which evoked response graph 402 is compared is used as a V1 vector-specific ER template. The V1-specific ER template may be used as a threshold criteria basis to subsequent recorded evoked responses along vector V1 to determine if the pacing pulses that produced the recorded evoked responses achieved local capture as well.

Figure 5:
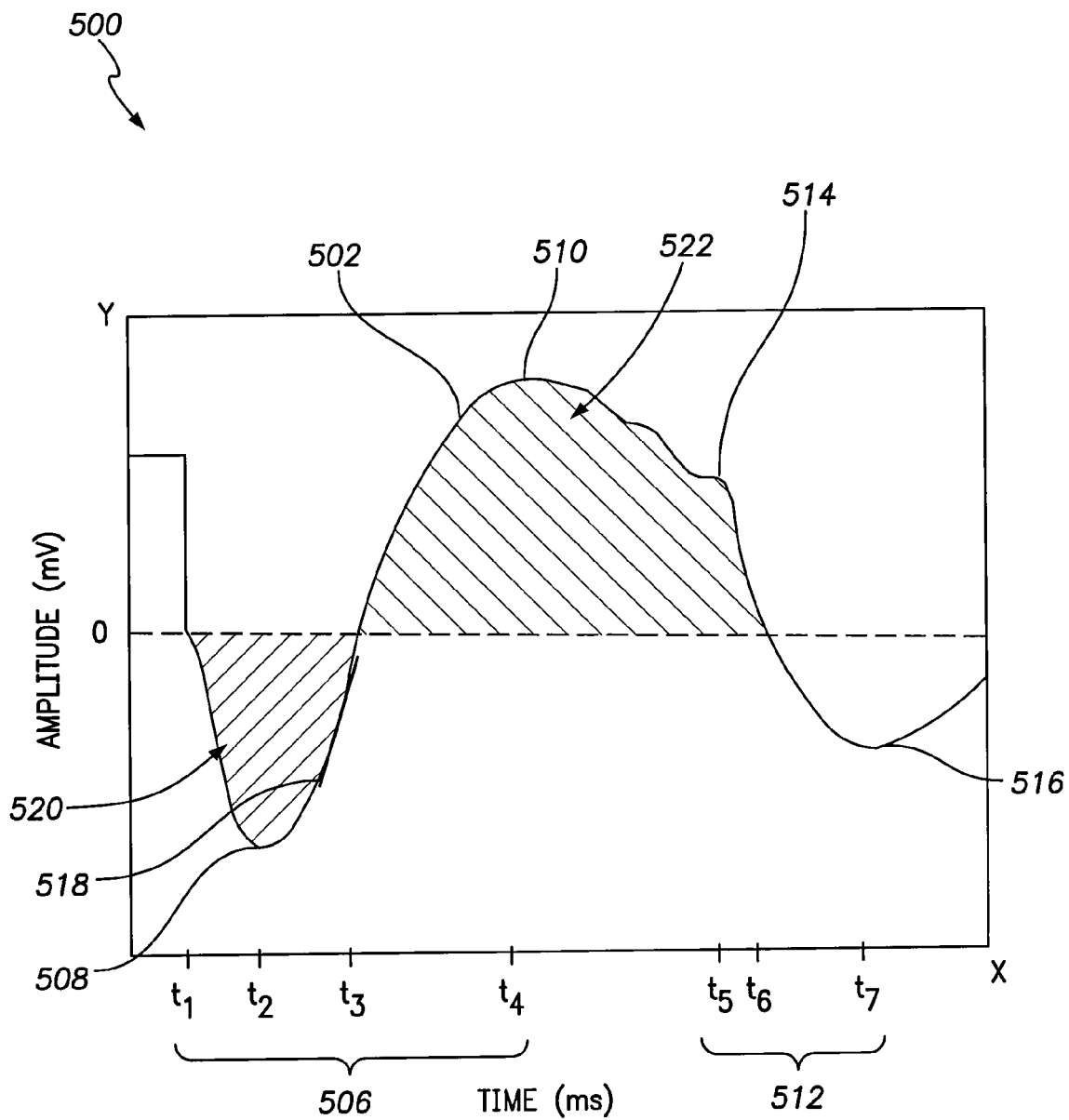
FIG. 5 shows an example graph plotting a data stream measured in connection with an evoked response.

FIG. 5 shows an example graph 500 plotting a data stream measured in connection with an evoked response. The data stream may be displayed on the graph 500 as a waveform 502 representative of the electrical activity in LV tissue (measured in millivolts (mV)) over time (measured in milliseconds (ms)) as sensed at a sensing channel. The graph 500 may be an IEGM graph. The electrical activity may be a potential difference measured over time between the electrodes that define the sensing channel. For example, when a pacing pulse is delivered over the vector D1-RVC, the electrodes D1 and RV coil 136 may immediately start sensing for the changes in electrical activity of the corresponding surrounding LV tissue regions in response to the pulse. The sensing channel may be the same as the pacing channel. Optionally, the sensing channel may be a different vector selected by the MSLV controller 165 than the selected pacing vector. If the pacing and sensing channels are different, the microcontroller 160 may control the ventricular pulse generator 172 to deliver a pacing pulse over the pacing vector, and at the same time or immediately after, the microcontroller 160 may control the ventricular sensing circuits 184 to receive sensing signals from the sensing electrodes.

The waveform 502 fluctuates between having a positive and a negative amplitude (e.g., above and below the baseline (y=0 mV)) as the depolarization wave propagates along the LV tissue. The shape of the waveform 502 is dependent on at least the pacing pulse output, the pacing site within the heart, the pacing vector, the sensing channel, scars or other irregularities in the heart muscle, artifacts or interferences from other pacing pulses, and the like. However, as mentioned above, the waveform 502 has several characteristics that may be used in comparing IEGMs, such as comparing recorded evoked responses to an ER template that represents a threshold criteria basis. The IEGM graph 500 is illustrative of an evoked response, and does not necessarily represent the evoked response of a pulse that achieved local capture of a proximate region of the myocardial tissue.

As shown in FIG. 5, a pacing event (e.g., delivery of a pacing pulse) occurs at time $t_0$ and a temporary pacing spike 504 in the waveform 502 is recorded in response. At time $t_1$, the pacing spike 504 quickly drops off into the negative region, where the wave enters the R-wave 506, which represents intrinsic ventricular depolarization. At time $t_2$, the recorded waveform 502 reaches the maximum negative amplitude 508 of the R-wave 506. At time $t_3$, the waveform 502 regains a positive amplitude, reaching a maximum positive amplitude 510 of the R-wave 506 at time $t_4$. The waveform 502 then progresses into a T-wave 512 following the R-wave 506. The T-wave 512 has a maximum positive amplitude 514 at $t_5$ and a minimum (e.g., maximum negative) amplitude 516 at $t_7$.

Plotted data streams of recorded evoked responses in the form of IEGMs may be compared to IEGMs of ER templates by comparing various segments and/or characteristics of the waveforms. For example, the R-waves 506 of two or more waveforms 502 may be compared, such as by comparing the maximum negative amplitude 508, the maximum positive amplitude 510, and the maximum upward slope 518 of the R-waves 506. In addition, the area under the slopes may be determined using integrals and used for comparison between IEGMs. For example, the area of the curve 520 above the negative section of the waveform 502 from time $t_1$ to $t_3$, the area of the curve 522 below the positive section from $t_3$ to $t_6$, and/or the value of both areas 520, 522 combined may be used to compare IEGMs. Furthermore, two or more IEGMs may be compared by performing a waveform correlation, which is a computed measure of similarity of at least two waveforms 502 over time, as known in the art. In an embodiment, the comparison of these characteristics of IEGMs may be performed automatically by the ICS system 100 as controlled by the autocapture algorithm of one or more embodiments described herein.

Referring back to 306 of FIG. 3, the recorded data streams measured in connection with the evoked responses are compared to at least one ER template to determine whether one or more of the pacing pulses achieved local capture over the corresponding pacing vectors. Using one or more of the various characteristics of IEGMs discussed above, the determination of whether local capture was achieved may be made if the recorded data stream of an evoked response exceeds a designated similarity threshold of a corresponding template. For example, local capture may be determined if a waveform correlation between waveforms 502 (shown in FIG. 5) of an evoked response and an ER template is higher than 0.8. As such, a pacing pulse over vector D1-RVC may be determined to have achieved local capture if the evoked response has a recorded waveform that correlates to 0.9 of the waveform of the corresponding ER template. A correlation of 0.9 indicates that similarity is 90%. Likewise a designated similarity threshold may be used to determine local capture when comparing areas, slopes, and/or maximum amplitudes of the waveforms. The similarity threshold may be specific to the characteristic being compared. For example, comparing maximum positive amplitudes 510 of R-waves 506 may require a higher designated similarity threshold than for comparing waveform correlations in order to determine achievement of local capture.

Alternatively, or in addition, a tested evoked response may be determined to have achieved capture if the compared characteristic of the waveform (e.g., slope, min/max amplitude, area, etc.) is greater than the corresponding characteristic on the ER template. For example, plotted data of an evoked response with a greater area under the curve 522 (shown in FIG. 5) between times $t_3$ and $t_6$ than the ER template may indicate that the pacing pulse had more than enough energy to achieve local capture. The designated threshold may be determined by a clinician. The designated similarity threshold also may be vector-specific. Furthermore, the designated threshold may be a predefined parameter stored within the autocapture algorithm, and/or may be adjusted, such as by the clinician.

Referring now back to FIG. 4, by comparing the plotted data streams 402-408 recorded in connection with corresponding evoked responses to the ER template 410, it may be determined, for example, that evoked response graphs 402 and 404 indicate local capture while graphs 402 and 404 indicate lack of local capture. By performing a waveform correlation, the waveforms 412 and 414 within graphs 402 and 404, respectively, have a high correlation to the waveform 420 of the ER template 410, which may exceed the designated similarity threshold for waveform correlation. On the other hand, the waveforms 416 and 418 within graphs 406 and 408, respectively, do not correlate highly with the waveform 420, likely not exceeding the designated similarity threshold. As a result, it may be determined that the pacing pulses along vectors V1 and V2 associated with evoked response graphs 402 and 404, respectively, achieved local capture, while the pacing pulses along vectors V3 and V4 did not achieve local capture.

The same result may be reached by comparing other characteristics of the waveforms such as areas under the curves, min/max amplitudes, max upward slope, etc. As shown in FIG. 4, the areas under the positive curve 422 and 424 associated with respective local capture vectors V1 and V2 are more similar to the area under the curve 430 of the ER template 410 than the areas 426 and 428 associated with respective vectors V3 and V4. The value of the areas 422 and 424 may fall within a designated similarity threshold of the area 430, indicating that local capture was achieved. Optionally, the areas 422 and 424 may exceed the area 430 of the ER template, which would also indicate that local capture was achieved by the corresponding pacing pulses. In contrast, the areas 426 and 428, as shown in FIG. 4, do not exceed the area 430, thus further indicating that the pulses over vectors V3 and V4 did not achieve local capture. In this illustrative example, the pulses over vectors V1 and V2 were determined to have achieved capture, unlike the pulses over vectors V3 and V4. However, based on various characteristics compared and designated thresholds used, it may be determined that all of the pulses locally captured, none of the pulses locally captured, or some other configurations of some pulses achieved local capture. For example, it may be determined that only the pulse delivered over vector V1 achieved local capture.

At 308, after comparing the recorded data streams measured in connection with the evoked responses to the at least one ER template to determine whether local capture was achieved by one or more of the pacing pulses, the pacing pulses are updated. The pulses may be updated by the PPU module 165b within the MSLV controller 165. The pacing pulses are updated in order to determine a local capture threshold for the corresponding pacing vectors. The local capture threshold is the minimum pacing output that achieves local capture for the respective pacing vector. As discussed above, the local capture thresholds may differ among the various pacing vectors. The local capture threshold for the corresponding pacing vectors is sought to be determined so as to allow pacing pulses delivered with a pacing output equal to or greater than the local capture threshold to achieve local capture while not wasting the limited energy resources. For example, when multiple pacing pulses are simultaneously paced along multiple corresponding vectors, the pacing pulses are updated to determine local capture thresholds for each of the pacing vectors, so pacing pulses during subsequent cardiac cycles achieve local capture while limiting the energy expelled to deliver the pulses.

As discussed further below with reference to FIG. 6, the pacing pulses may be updated by adjusting the pacing output of subsequent pacing pulses to "zero in" on the local capture threshold for the corresponding vectors. For example, if a pacing pulse delivered along a pacing vector did not achieve local capture, the pacing output of the next pacing pulse delivered along the pacing vector may be increased. Increasing the pacing pulse for the next cardiac cycle may achieve local capture during the next cycle, or at least will assist in determining the local capture threshold by zeroing in on the threshold. On the other hand, if a previous pacing pulse achieved local capture, the next pacing pulse output may be decreased in an attempt to determine the pacing output that achieves local capture while also conserves energy (e.g., which is the output at the local capture threshold). For example, although the previous pacing pulse achieved local capture, the pulse may have had a voltage that was higher than necessary to achieve local capture, so the excess energy was wasted. Since the method 300 involves multisite pacing, the pacing pulses may be updated individually based on the respective local capture determinations. Therefore, some pacing pulses may be updated to increase pacing output and other pacing pulses may be updated to decrease pacing output for subsequent cardiac cycles. As with the other operations in method 300, the autocapture algorithm that performs the method 300 may automatically update the pacing pulses at 308.

After the pacing pulses are updated, the method 300 returns to 302 where a next group of pacing pulses are delivered over the pacing vectors simultaneously. The method 300 repeats in order to narrow in on the local capture thresholds of the corresponding pacing vectors. In an embodiment, the pacing pulses are delivered simultaneously for multiple cardiac cycles until the local capture threshold for each of the pulsed pacing vectors is determined.

Figure 6:
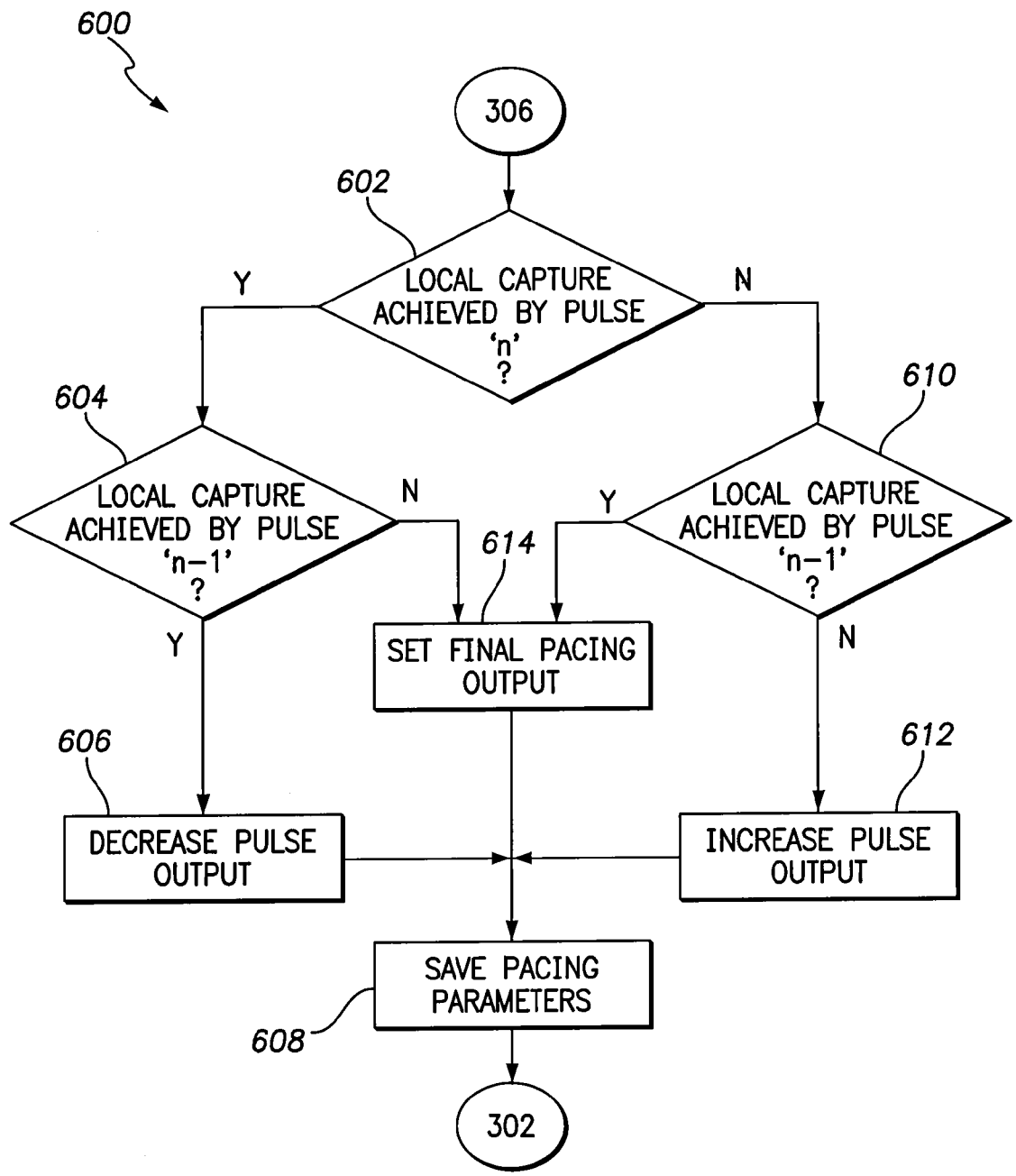
FIG. 6 is a flow chart for a method of updating pacing pulses to determine local capture thresholds of corresponding pacing vectors according to an embodiment.

FIG. 6 is a method 600 for updating pacing pulses to determine local capture thresholds of corresponding pacing vectors according to an embodiment. The method 600 may be used in conjunction with the method 300 of FIG. 3. More specifically, the method 600 may replace operation 308 in method 300. Therefore, after comparing evoked responses to one or more ER templates to determine if local capture was achieved by one or more pacing pulses over corresponding pacing vectors, as in 306 of FIG. 3, the flow of method 300 may proceed to 602 of method 600 in FIG. 6. As with method 300, method 600 may be performed by an implantable device, such as device 100 (shown in FIG. 1), and/or may be controlled by an algorithm. It is noted that the operations of method 600 are described with reference to a single pacing vector, but the autocapture algorithm may perform the same operations simultaneously for multiple pacing vectors.

At 602, a determination is made as to whether local capture has been achieved by pacing pulse 'n'. Pacing pulse 'n', as used herein, represents the current or most recent pacing pulse that has been delivered along a corresponding pacing vector. Where pacing pulse 'n' represents the most recent pacing pulse delivered, pacing pulse 'n−1', also used herein, represents the pacing pulse that precedes pacing pulse and pacing pulse 'n+1' is the pulse delivered after pacing pulse Therefore, 'n−1', 'n', 'n+1', etc. represent chronological events, such as chronological cardiac cycles. The determination of whether local capture has been achieved by pacing pulse may be made by comparing and/or correlating an evoked response to an ER template, as described in 306 of FIG. 3 (and FIGS. 4 and 5). Whether or not local capture has been achieved affects how the subsequent pacing pulse will be adjusted to narrow in on the local capture threshold for the respective vector. If local capture has been achieved by pulse 'n', flow of the method 600 moves along the branch denoted by "Y" to 604.

At 604, a determination is made as to whether local capture was achieved in response to pacing pulse 'n−1' (e.g., the previous pacing pulse) over the same pacing vector. The determination for the previous pacing pulse would have used the same approach as in 602 to determine whether local capture was achieved by the most recent pacing pulse. If local capture has been achieved by pulse 'n−1', flow of the method 600 moves along the branch denoted by "Y" to 606.

Flow of the method 600 has reached 606 because both of the last two pacing pulses delivered over the pacing vector have achieved local capture. As such, at 606, the pacing output is decreased in order to limit the amount of excess energy above the local capture threshold that is being used. The pacing output may be decreased by a defined step amount. For example, the step amount may be between 0.1 and 0.4 V, such as 0.25 V. In an embodiment, the local capture threshold is determined by first starting with a high pacing output (e.g., 2 V) that is selected to assure local capture of the surrounding LV tissue. After each pacing pulse that achieves local capture, the pacing output of the next pulse (e.g., 'n+1' pulse) is decreased by the step amount in order to zero in on the local capture threshold while still achieving local capture during at least most of the cardiac cycles. After decreasing the pulse output at 606, the method proceeds to 608.

At 608, the updated pacing parameters are saved. Therefore, if a previous pacing pulse with an output of 1 V achieved local capture (and the prior pulse did so as well), and the pulse output was lowered by the step 0.25 V to 0.75 V, all of this information may be saved. The pacing parameters may be stored on the memory 194 (shown in FIG. 2) of the device 100 (shown in FIG. 2), within the microcontroller 160 (shown in FIG. 2), and/or may be transmitted externally from the device 100. Relevant pacing parameters (specific to a single pacing vector) to be saved may include the output (1 V) of the previous pulse, the result of the previous pulse (e.g., whether local capture was achieved), the adjusted output (e.g., 0.75 V) of the next pulse, the pacing vector over which the pulses are being delivered, the sensing channel over which the evoked responses are being monitored, the timing between the pulses, and the like. At 608, the pacing parameters for multiple pacing vectors may be saved.

Referring back to 602, if local capture was not achieved by pulse 'n', the flow of the method 600 proceeds to 610. At 610, a determination is made as to whether local capture was achieved by pulse 'n−1'. If not, then the previous two pacing pulses over the pacing vector failed to achieve local capture of the surrounding LV tissue. Flow of the method 600 proceeds to 612, where the pulse output is increased. In an embodiment, the local capture threshold is determined by first starting with a low pacing output (e.g., 0.2 V) that is selected knowing that local capture of the surrounding LV tissue will not be achieved. After each pacing pulse that does not achieve local capture, the pacing output of the next pulse (e.g., 'n+1' pulse) is increased by a step amount (e.g., 0.25 V) in order to zero in on the local capture threshold. Since multiple consecutive pacing pulses fail to achieve local capture (e.g., fail to desirably control the contraction of the surrounding myocardium tissue), a backup pulse may be provided to stimulate the heart tissue after it is determined that a pacing pulse did not achieve local capture. The backup pulse protects the patient from deleterious health effects caused by pulses that fail to achieve local capture. Therefore, the method 600 is designed to accommodate local capture threshold determination that gradually steps-up a low pacing output as well as one that gradually steps-down a high pacing output (with reference to 604 and 606). After the pulse output is increased by the step amount, flow of the method 600 proceeds to 608, where the pacing parameters are saved.

Referring now back to 604, if it is determined that the current (e.g., 'n') pacing pulse has achieved local capture, but the previous pulse (e.g., 'n–1') failed to achieve local capture, then flow of the method 600 proceeds along the branch denoted "N" to 614. For example, if the previous pacing pulse during the prior cardiac cycle failed to achieve local capture (and assuming the pulse before that previous pulse also failed to capture), then during the prior cardiac cycle flow of the method 600 would have proceeded to 612 where the pacing output would have been increased. As such, the prior pacing pulse had an output that was below the local capture threshold, so the pacing output was increased for the now current pacing pulse. Since the current pacing pulse, which is only a step amount greater than the previous pulse, has achieved local capture, then the local capture threshold is likely between the previous two pacing outputs.

Referring now back to 610, flow of the method 600 also proceeds to 614 if it is determined that the current (e.g., 'n') pacing pulse failed to achieve local capture, but the previous pulse (e.g., 'n–1') achieved local capture. This path is shown by proceeding from 602 along the branch denoted "N" to 610, and then proceeding along the branch denoted "Y" to 614. This path may be followed when determining the local capture threshold by gradually stepping-down a high pacing output. For example, the 'n–1' pulse at 610 achieved local capture. Therefore, during the prior cardiac cycle, the method 600 proceeded through 604 to 606, where the pulse output was once again decreased by a step amount. However, the 'n' pulse failed to achieve local capture at 602. As such, the current pacing output is lower than the local capture threshold, but the prior pulse output was greater than the local capture threshold.

In an embodiment, the local capture threshold is designated as the pacing output that achieved local capture and is one step value above a pacing output that did not achieve local capture. For example, when the threshold is determined by stepping up consecutive pacing outputs until local capture is achieved, the local capture threshold is designated as the output for pulse 'n', which achieved local capture. On the other hand, when the threshold is determined by stepping down consecutive pacing outputs until local capture is no longer achieved, the local capture threshold is designated as the output for pulse 'n–1', which also achieved local capture. Optionally, the accuracy of the determination may be verified by retesting the last two pacing outputs to verify, as an example, that the output of pulse 'n' achieves local capture while the output of pulse 'n–1', being only a step below the output of pulse 'n', does not capture. In addition, the local capture threshold may be determined with more precision by decreasing the step size. For example, instead of using a step size of 0.25 V, the step size may be reduced to 0.1 V once the threshold is narrowed to within the guideposts determined above using the larger step size.

At 614, once the local capture threshold for a pacing vector is determined, the final pacing output for the pacing vector is set. The final pacing output may be set by adding a designated safety margin to the local capture threshold. The designated safety margin may be a voltage that is the same amount as a step size used to determine the local capture threshold. For example, the safety margin may be 0.25 V. Optionally, the safety margin may be more or less than the step size. The addition of the designated safety margin accounts for the daily variations in the local capture threshold. The safety margin thus ensures that pacing pulses delivered at the final pacing output over the corresponding pacing vector reliably achieve local capture each cardiac cycle.

After setting the final pacing output for the pacing vector, flow proceeds to 608, where the pacing parameters are saved. The pacing parameters include the final pacing output and the identification of the corresponding pacing vector. The pacing parameters may also include timing, amount of added safety margin, and the like, as well as parameters for other pacing vectors.

In an embodiment, four pacing pulses are delivered simultaneously over corresponding LV pacing vectors. Once the evoked responses are recorded and compared to the corresponding one or more ER templates to determine if local capture was achieved by one or more of the pulses, the method 600 is performed for each of the four pacing vectors. The pacing vectors may have different local capture thresholds. Therefore, even if the respective pulse outputs are identical for a given group of simultaneous pulses, the flow through method 600 may be different for different pacing vectors. For example, in response to four simultaneous pacing pulses in a cardiac cycle (e.g., 'n') each having a pacing output of 0.75 V, one pacing pulse may achieve local capture, while the other three do not achieve local capture. Therefore, during a next cardiac cycle (e.g., 'n+1'), the pacing output for the one pacing vector that previously achieved local capture is reduced, while the pacing outputs for the other three vectors are increased. Continuing this example, during the n+1 cycle, only one of the three vectors that previously failed to achieve local capture now achieved local capture, so the pacing outputs for the individual vectors for cycle 'n+2' are adjusted accordingly. Therefore, the pacing vectors may take independent paths through the process 600 over multiple cardiac cycles when determining the respective local capture thresholds. However, the pacing parameters for all of the pacing vectors may be saved at 608 for each cardiac pacing cycle. Saving the pacing parameters allows the microcontroller 160 (shown in FIG. 2), as well as a clinician, to track the progress of each of the pacing vectors during the automatic local capture threshold determination process.

After the pacing parameters are saved, the method 600 returns to 302 of method 300 (shown in FIG. 3). At 302, the updated pacing pulses (e.g., having updating pacing outputs) are delivered over the corresponding pacing vectors simultaneously. The method 300 then repeats as described above. In an embodiment, once the local capture threshold is determined for one of the pacing vectors and its final pacing output is set and saved, the pacing vector no longer proceeds through 308 (e.g., process 600) in subsequent cardiac pacing cycles. Once, the final pacing output is set for a respective pacing vector, it is not necessary to continue updating the pacing output of pacing pulses delivered over that vector. Instead, during the next simultaneous pacing delivery at 302, that pacing vector is paced at its final pacing output. For example, that vector may be paced at its final pacing output until all of the final pacing outputs of all of the other pacing vectors have been set. The algorithm may therefore only validate the local capture thresholds for the pacing vectors that have not yet been determined.

In an alternative embodiment, once the local capture threshold for one of the pacing vectors is determined and the final pacing output set, a pacing pulse is not delivered over that pacing vector during subsequent cardiac cycles until the local capture threshold corresponding to each of the pacing vectors is determined. Therefore, during the subsequent cardiac cycles, at 302 pacing pulses may not be delivered over all pacing vectors simultaneously, but rather all of the pacing vectors that still need to validate the local capture threshold. The pacing vectors that have a set final pacing output may be switched to a default value while the remaining autocapture operations are performed. A backup pulse may be used to provide stimulation when some of the electrodes are being unused.

Although some embodiments herein are directed to delivering simultaneous MSLV pacing pulses, in an alternative embodiment the multiple pulses may be separated by a certain duration (e.g., instead of simultaneously). For example, one or more of the pulses may be offset from another pulse by 10 ms.

It is to be understood that the above description is intended to be illustrative, and not restrictive. For example, the above-described embodiments (and/or aspects thereof) may be used in combination with each other. In addition, many modifications may be made to adapt a particular situation or material to the subject matter of an embodiment described herein without departing from scope of the teachings herein. While the dimensions, types of materials and coatings described herein are intended to define parameters of one or more embodiments, they are by no means limiting and are exemplary embodiments. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implantable cardiac stimulation (ICS) system including a lead having multiple electrodes implantable proximate to a patient's left ventricular (LV) chamber, the system comprising:

a pacing pulse delivery (PPD) module configured to simultaneously deliver multiple pacing pulses over corresponding left ventricular pacing vectors, the pacing vectors defined by electrodes proximate to the LV chamber;

an evoked response recording (ERR) module configured to record evoked responses that are responsive to the pacing pulses, the evoked responses associated with the corresponding pacing pulses and measured over separate corresponding sensing channels;

an evoked response comparison (ERC) module configured to compare the evoked responses to at least one template, the at least one template representing local capture of a local LV tissue region along one or more of the corresponding pacing vectors, the comparison used to determine whether the pacing pulses achieved local capture along the corresponding pacing vectors; and a pacing pulse update (PPU) module configured to update at least one of the pacing pulses or the pacing vectors based on the comparison of the evoked responses to the at least one template in order to determine a local capture threshold for the corresponding pacing vectors.

2. The ICS system of claim 1, wherein the at least one template is representative of an evoked response responsive to a pacing pulse that is determined by a clinician to achieve local capture.

3. The ICS system of claim 1, wherein the ERC module is configured to compare the evoked responses to a single template that represents local capture.

4. The ICS system of claim 1, wherein the ERC module is configured to compare the evoked responses to different templates, the different templates representative of local capture along the respective pacing vectors.

5. The ICS system of claim 1, wherein the ERC module is configured to perform a waveform correlation between the evoked responses and the at least one template.

6. The ICS system of claim 1, wherein the ERC module is configured to compare at least one of an area under a curve, a maximum amplitude of a curve, or a maximum slope of a curve within a waveform represented in an intracardiac electrogram.

7. The ICS system of claim 1, wherein the PPU module is configured to increase a pacing output of a next pacing pulse over one pacing vector if the pacing pulse did not achieve local capture along the pacing vector, or to decrease the pacing output of the next pacing pulse over the pacing vector if the pacing pulse achieved local capture along the pacing vector.

8. The ICS system of claim 1, wherein the PPD module is configured to simultaneously deliver the pacing pulses over the corresponding pacing vectors for multiple cardiac cycles until the local capture threshold for each of the pacing vectors is determined.

* * * * *